(12) United States Patent
Ryan et al.

(10) Patent No.: US 10,813,778 B2
(45) Date of Patent: Oct. 27, 2020

(54) AXIAL LOCK AND RELEASE STENT DEPLOYMENT SYSTEM

(71) Applicant: Cook Medical Technologies LLC, Bloomington, IN (US)

(72) Inventors: Michael Ryan, Limerick (IE); Gerard Treacy, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 184 days.

(21) Appl. No.: 16/122,654

(22) Filed: Sep. 5, 2018

(65) Prior Publication Data

US 2019/0000651 A1 Jan. 3, 2019

Related U.S. Application Data

(62) Division of application No. 15/096,709, filed on Apr. 12, 2016, now abandoned.

(60) Provisional application No. 62/146,850, filed on Apr. 13, 2015.

(51) Int. Cl.
*A61F 2/90* (2013.01)
*A61F 2/95* (2013.01)

(52) U.S. Cl.
CPC .................. *A61F 2/90* (2013.01); *A61F 2/95* (2013.01); *A61F 2002/9505* (2013.01); *A61F 2002/9511* (2013.01); *A61F 2230/001* (2013.01); *A61F 2250/001* (2013.01); *A61F 2250/0039* (2013.01)

(58) Field of Classification Search
CPC ........ A61F 2002/9505–9665; A61F 2230/001; A61F 2250/001; A61F 2250/0039; A61F 2/90; A61F 2/95–97; A61F 2002/9511
See application file for complete search history.

(56) References Cited

U.S. PATENT DOCUMENTS

| | | |
|---|---|---|
| 6,270,520 B1 | 8/2001 | Inoue et al. |
| 7,147,657 B2 | 12/2006 | Chiang et al. |
| 2002/0040236 A1 | 4/2002 | Lau et al. |
| 2003/0050684 A1 | 3/2003 | Abrams et al. |
| 2003/0233140 A1 | 12/2003 | Hartley et al. |
| 2006/0190070 A1* | 8/2006 | Dieck ................ A61F 2/97 623/1.12 |
| 2017/0165066 A1* | 6/2017 | Rothstein ............ A61F 2/2418 |

FOREIGN PATENT DOCUMENTS

| | | |
|---|---|---|
| EP | 2749251 | 2/2014 |
| EP | 2735283 | 5/2014 |
| WO | 1996/0243308 | 8/1996 |
| WO | 2011/159751 | 12/2011 |
| WO | 2016/168176 | 10/2016 |

OTHER PUBLICATIONS

International Search Report and Written Opinion for PCT/US2016/027092, dated Jun. 17, 2016, 14 pp.

* cited by examiner

*Primary Examiner* — Katherine M Shi
*Assistant Examiner* — Alyssa M Keane
(74) *Attorney, Agent, or Firm* — Brinks Gilson & Lione

(57) ABSTRACT

The present disclosure relates to stents and methods of delivering and deploying the same. The stents include fasteners about their periphery and when the stent is radially compressed, the fasteners come into alignment such that a device may be placed through openings in the fasteners to hold the stent in the radially compressed configuration. When the device is removed from the openings, the stent may expand.

11 Claims, 3 Drawing Sheets

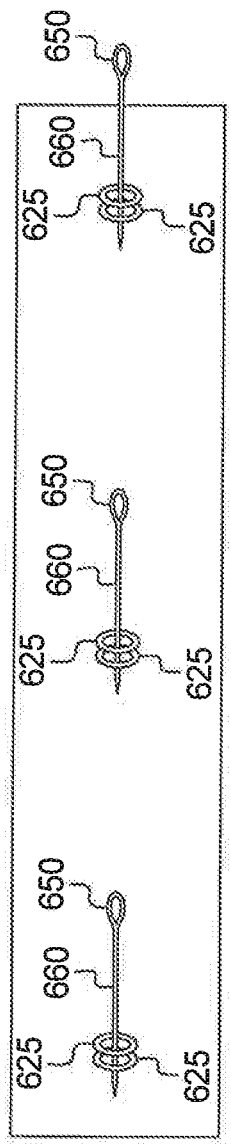
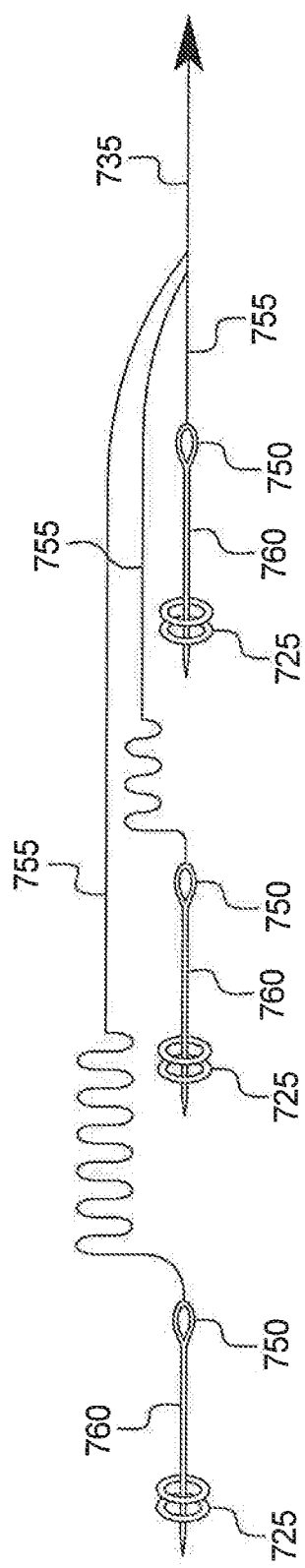

AXIAL LOCK AND RELEASE STENT DEPLOYMENT SYSTEM

BACKGROUND

1. Field of the Invention

The present disclosure generally relates to medical devices. More particularly, the disclosure relates to stents and methods of delivering and deploying the stents.

2. Description of the Related Art

Stents have become a common alternative for treating vascular conditions because stenting procedures are considerably less invasive than other alternatives. As an example, stenoses in the coronary arteries have traditionally been treated with bypass surgery. However, stenting procedures are performed transluminally and do not require open surgery. Thus, recovery time is reduced and the risks of surgery are minimized.

One common type of stent used in medical procedures is the self-expanding stent. Self-expanding stents are usually made of shape memory materials or other elastic materials that act like a spring. Self-expanding stents are increasingly being used by physicians because of their adaptability to a variety of different conditions and procedures. Typical metals used in this type of stent include nitinol and stainless steel. However, other materials may also be used. To facilitate stent implantation, self-expanding stents are normally installed on the end of a delivery catheter in a low profile, compressed state. The stent is typically inserted into a sheath at the end of the catheter, which restrains the stent in the compressed state. The stent and catheter assembly is then guided along a guide wire to the portion of the vessel to be treated. Once the catheter and stent are positioned adjacent the portion of the vessel to be treated, the stent is released by pulling, or withdrawing, the sheath rearward.

One problem that exists with conventional self-expanding stent deployment systems is that the longitudinal force imposed upon the delivery sheath can be relatively high. Typically, an inner tube disposed proximal to the stent is held steady to longitudinally restrain the stent while a proximal end of the delivery sheath is retracted, thereby exposing the stent. However, as the proximal end of the delivery sheath is being pulled, a significant build-up of energy may occur along the length of the delivery sheath due to friction between the delivery sheath and the stent. In particular, the act of deployment typically imposes a stretch on the overall length of the delivery sheath, and thus, results in a substantial axial compressive force on the overall length of the inner tube. The stored energy in the delivery sheath and/or inner tube may be suddenly released, causing the stent to move forward unexpectedly, e.g., "jump" forward, leading to inaccurate placement of the stent in a vessel.

Moreover, the significant forces imposed upon the delivery sheath containing the self-expanding stent, and/or the inner tube disposed proximal to the stent, may lead to various system failures. For example, the delivery sheath itself may be stretched beyond its maximum ability and may not recover elasticity or may break in half, various fittings may become disengaged due to the forces imposed, the inner tube may become overly compressed into an "accordion" shape, and so forth.

Problematically, the energy build-up within the delivery sheath and inner tube may be even more affected as the length of the delivery system is increased. Since relatively long self-expanding stents, e.g., having lengths between 200 to 300 mm, may become prevalent in newer devices, the problem of energy build-up in the delivery sheath and inner tube may become a larger concern. Accordingly, there is a need for improved methods of delivering and deploying self-expanding stents.

BRIEF SUMMARY

The present disclosure relates to stents and methods of delivering and deploying the stents. In one embodiment, a stent is disclosed comprising a proximal portion, a mid-section, and a distal portion, wherein one or more of the proximal portion, mid-section, and distal portion comprises a plurality of fasteners.

In another embodiment, a method of deploying a stent at a target location is disclosed. The method comprises providing a stent in a radially compressed configuration, the stent comprising a plurality of fasteners, each fastener of the plurality of fasteners comprising an opening, wherein the openings of each fastener are in alignment in a lumen of the radially compressed stent, and further wherein a rod is disposed through the openings of each fastener. The method also comprises the steps of placing the stent at the target location, proximally withdrawing the rod from the openings of the fasteners, allowing the stent to expand, and deploying the stent at the target location.

In an additional embodiment, a method of deploying a stent at a target location is disclosed. The method comprises providing a stent in a radially compressed configuration, a distal portion of the stent comprising a first plurality of fasteners, a mid-section of the stent comprising a second plurality of fasteners, and a proximal portion of the stent comprising a third plurality of fasteners, each fastener comprising an opening, wherein the openings of each fastener of the first plurality of fasteners are in alignment, the openings of each fastener of the second plurality of fasteners are in alignment, and the openings of each fastener of the third plurality of fasteners are in alignment, and further wherein a first release pin is disposed through the openings of each fastener of at least the first plurality of fasteners and a second release pin is disposed through the openings of each fastener of at least the third plurality of fasteners, the first release pin being attached to a distal portion of a rod by a first suture and the second release pin being attached to the distal portion of the rod by a second suture. The method also comprises the steps of placing the stent at the target location, proximally withdrawing the rod, thereby causing the first and second release pins to withdraw from the openings of the fasteners, allowing the stent to expand, and deploying the stent at the target location.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which:

FIG. 6 shows a stent comprising three release pins disposed through the openings of six fasteners; and FIG. 7 shows three release pins being connected to a rod by sutures having different lengths.

DETAILED DESCRIPTION

Figure 1:
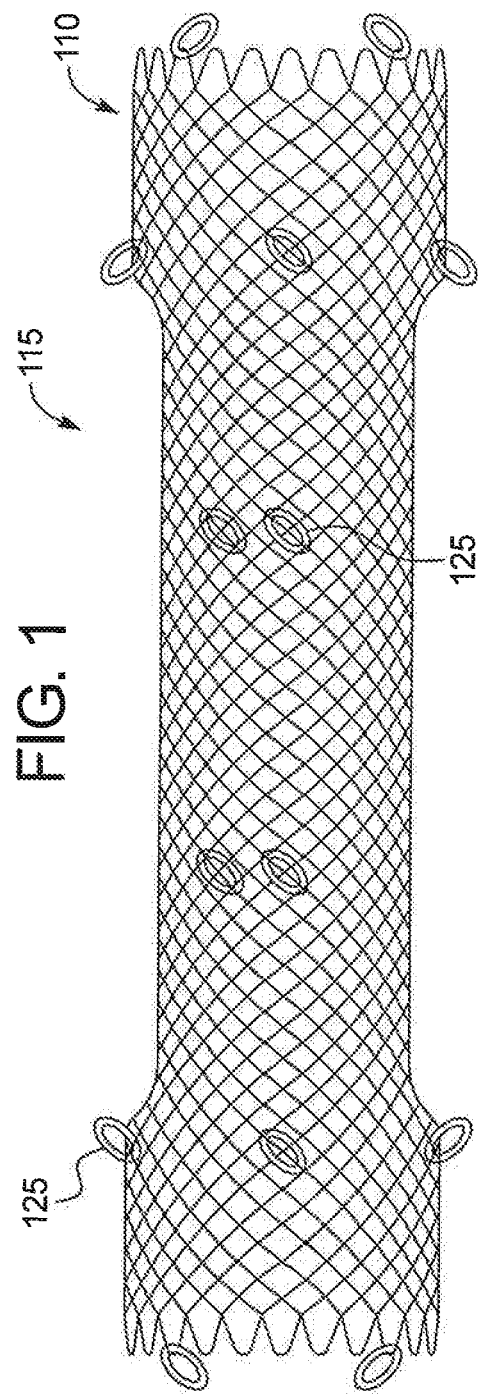
FIG. 1 shows a stent in its expanded configuration comprising a plurality of fasteners.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as conventional fabrication and assembly.

The present disclosure relates to stents, such as self-expanding stents, and methods for delivering and deploying the same. In accordance with FIG. 1, a stent is shown in the expanded configuration including a distal portion (110), a mid-section (115), and a proximal portion (120). As depicted, the stent also comprises a plurality of fasteners (125), which are useful for holding the stent in its radially compressed configuration. The fasteners (125) may be placed at any location along the body of the stent. In some embodiments, the proximal portion (120), the mid-section (115), and the distal portion (110) comprise a plurality of fasteners (125). In other embodiments, only one or two of the proximal portion (120), mid-section (115) and distal portion (110) comprise a plurality of fasteners (125).

When referring to "a plurality" of fasteners, it is to be understood that this means two or more fasteners. There is no upper limit to the number of fasteners the stent may comprise. As such, a plurality can include anywhere from, for example, 2 fasteners to 100 fasteners or more, such as from about 6 fasteners to about 50 fasteners or from about 9 fasteners to about 25 fasteners. For example, the proximal portion (120) of the stent may comprise 2-8 fasteners, such as 4 fasteners, the mid-section (115) may comprise 2-8 fasteners, such as 4 fasteners, and the distal portion (110) may comprise 2-8 fasteners, such as 4 fasteners.

The periphery of the stent comprises the fasteners. For example, in FIG. 2, the periphery of an end of the stent is shown in its expanded configuration comprising 4 fasteners (225). In this embodiment, the fasteners (225) are depicted as rings but the fasteners are not limited to rings and may instead include, for example, square shapes, triangular shapes, U-shapes, or any other configuration that can be secured by a rod.

In some embodiments, the fasteners comprise rings (or other shaped structures having openings therein, such as triangles or squares) and such rings are added onto an existing stent structure. In one illustrative example, a ring may be configured similarly to a ring that holds a house or car key, whereby a length of material having a proximal and a distal end is formed into a circular shape and the proximal and distal ends are not joined together but instead overlap. In other embodiments, a wire may be weaved or wound around an existing stent structure forming various loops or other shapes having openings, such as U-shapes, within the inner diameter of the stent. Alternatively, to create the fasteners, one may form U-shaped loops on the inside of the stent mesh with the existing stent wire while the stent is being woven.

Figure 2:
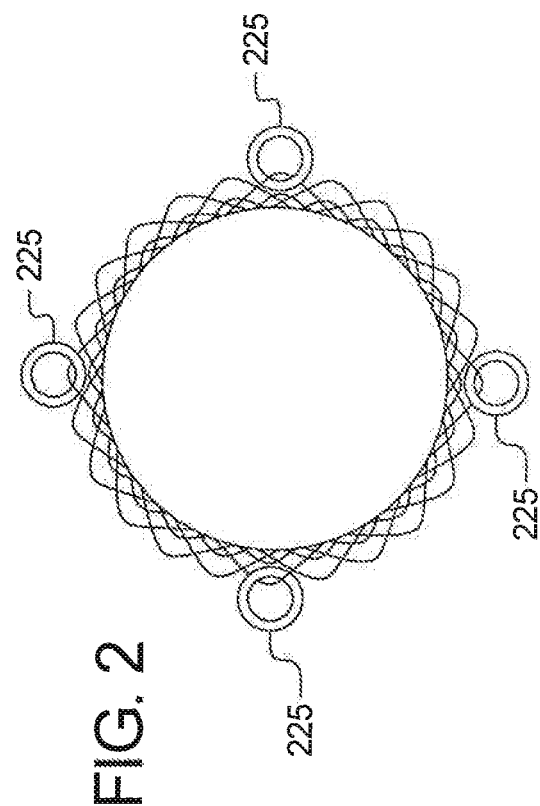
FIG. 2 shows an end of a stent in its expanded configuration comprising four fasteners.

Regardless of how they are formed, the fasteners (225) may be placed anywhere along the periphery of the body of the stent. In FIG. 2, the fasteners are placed near the 12 o'clock position on an end of the stent, near the 3 o'clock position, near the 6 o'clock position, and near the 9 o'clock position. No matter where the fasteners are placed along the body of the stent, once the stent is urged into its radially collapsed configuration, openings or lumens of the fasteners align. For example, if the fasteners comprise rings, the rings become concentric.

Figure 3:
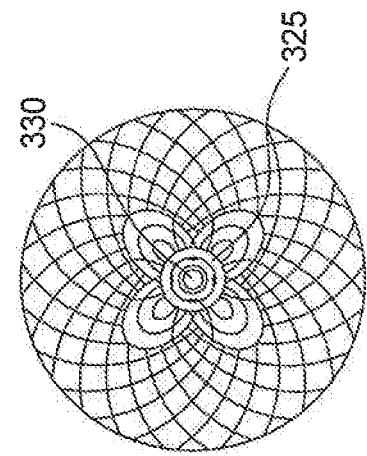
FIG. 3 shows an end of a stent in its radially compressed configuration with the openings of each fastener in alignment.
Figure 4:
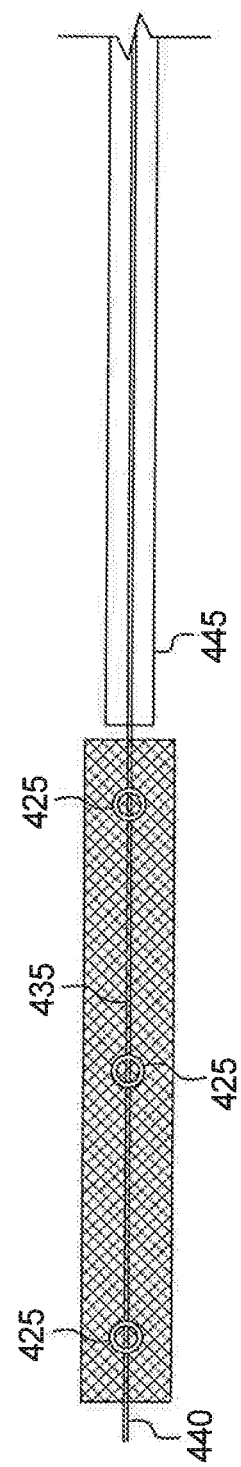
FIG. 4 shows a radially compressed stent having a rod disposed in the openings of each fastener.

FIG. 3. depicts an end of the stent shown in FIG. 2 in its radially compressed configuration. As can be seen, the opening/lumen (330) of each ring (325) aligns near the center of the stent lumen such that, for example, axial placement of a rod therethrough will lock/hold the stent in the radially compressed configuration, as can be seen in FIG. 4. The diameter of the openings (330) is not particularly limited and can generally be selected depending upon the diameter of the rod to be placed therethrough. In some embodiments, the diameter of a fastener may be from about 1 mm to about 4 mm or from about 2 mm to about 3 mm. If the diameter is too big, the stent will not completely compress. If the diameter is too small, there may be difficulties when trying to align the fasteners to allow placement of a rod through the openings thereof. The inner diameter of the fastener is generally slightly larger than the outer diameter of the rod placed therethrough. For example, if the inner diameter of the fastener is about 3 mm, then the outer diameter of the rod portion placed therethrough may be from about 2.5 mm to about 2.99 mm. In most embodiments, the outer diameter of the portion of the rod placed through the opening in the fastener is about 0.5 mm, 1 mm, 1.5 mm, 2 mm, 2.5 mm, 3 mm, etc., smaller than the inner diameter of the fastener.

Figure 5:
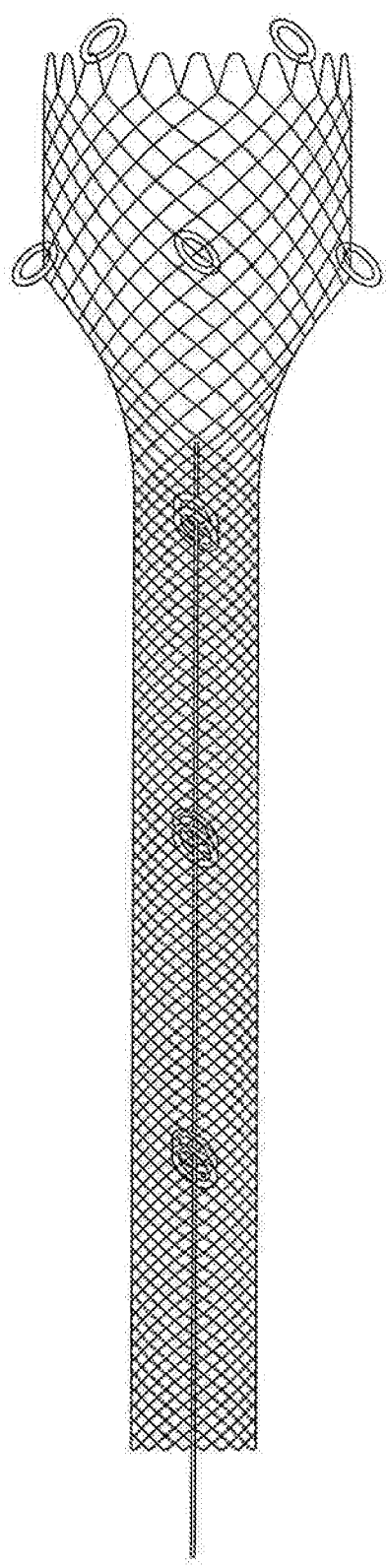
FIG. 5 shows a stent having one end in the expanded configuration and the opposite end and mid-section in a radially compressed configuration.

In FIG. 4, fasteners (425) are shown having aligned openings near a center portion of the stent lumen. A rod (435) is disposed in the opening of each fastener (425) to hold the stent in the compressed configuration. Removal of the rod (435) allows the stent to expand. In some embodiments, different sections of the stent may expand at different times. For example, when the distal end (440) of the rod is proximally withdrawn through the distal-most ring or distal-most plurality of rings, the distal end of the stent will open but a mid-section and proximal portion of the stent will remain compressed (see FIG. 5). As the distal end (440) of the rod continues to be proximally withdrawn, the stent will continue to expand.

The length of rod (435) is not critical and can generally be selected depending upon the length of the stent. In some embodiments, the stent and the rod have substantially the same length. In other embodiments, the length of the rod is less than the length of the stent or greater than the length of the stent.

In some embodiments, rod (435) is hollow, comprising a lumen or passageway therein, and its mid-section and/or proximal portion are disposed within a lumen or passageway of an outer tube (445). The distal end (440) of the rod can be passed over a wire guide to help guide the stent to the desired location in the body. A proximal end of the stent may contact a distal end of the outer tube (445), which may help keep the stent in place as the rod is proximally withdrawn. The outer diameter of outer tube (445) may be substantially equal to, smaller than, or larger than, the outer diameter of the stent in its compressed configuration. Outer tube (445) is connected to a handle at its proximal end and the proximal end of rod (435) may also be connected to the handle or a component thereof. When the handle is manipulated by a user, the rod (435) is proximally withdrawn, thereby disengaging the fasteners (425) and allowing the stent to expand. Any known handle may be used.

In some embodiments, the fasteners may comprise rings or other shapes having openings therein, such as triangles, squares, etc. For example, in FIG. 6, a stent is shown in a radially compressed configuration comprising a plurality of rings (625). The rings (625) are concentric so that each lumen or opening thereof is in alignment. A rod or any other device may be placed through the opening of each ring. In FIG. 6, three release pins (660) having eyes (650) similar to a sewing needle are placed through the openings of each ring. Although the stent of FIG. 6 is shown having three release pins (660), any number of release pins may be present. For example, the stent may comprise one release pin disposed through the opening of each plurality of concentric fasteners. In other embodiments, the stent may comprise from about two release pins to about six or more release pins. The number of release pins may dictate the number of sections of the stent that may be expanded separately.

For example, in FIG. 6, at least three different sections of the stent may be expanded separately since there are three different release pins. If only the distal-most release pin is removed and the other two release pins are kept in place in the ring openings, the distal portion of the stent will expand and the mid-section and proximal portion of the stent will remain compressed. If the release pin of the mid-section is then removed, the mid-section of the stent will expand but the proximal portion will remain compressed since that release pin has not yet been removed.

Removal of the release pin(s) may be accomplished by any means available. An illustrative, non-limiting example can be found in FIG. 7. FIG. 7 shows the same stent/release pin configuration as depicted in FIG. 6 except the stent is not shown. A distal portion of rod (735) may be disposed within the lumen of the stent and a proximal portion of the rod may be joined to a handle that can be manipulated by the user. In FIG. 7, the distal end of rod (735) comprises three sutures (755). The sutures (755) may be connected to a distal portion or distal end of the rod by any known means, such as using an adhesive, welding, soldering, etc.

The composition of the sutures (755) is not limited and they can comprise any suitable materials, such as various types of polymers, plastics, metals, etc. The sutures may be flexible or at least comprise one or more portions that are flexible. The distal end of the rod (735) may comprise any number of sutures. In some embodiments, the number of sutures is equivalent to the number of release pins. Moreover, each suture can be configured to have any desired length. For example, all sutures may comprise different lengths, some sutures may comprise the same length, or all sutures may comprise the same length.

The sutures (755) depicted in FIG. 7 comprise different lengths. For example, the suture (755) associated with the proximal-most release pin (760) comprises the shortest length. There is substantially no slack in the suture between the point where it connects/attaches to eye (750) and the point where it attaches/connects to the distal end of rod (735). The suture (755) associated with the middle release pin (760) comprises a length which is longer than the length of the suture associated with the proximal-most release pin. Moreover, the suture associated with the distal-most release pin comprises a length which is longer than the length of the suture associated with the middle release pin.

In this configuration, if rod (735) was proximally withdrawn a first distance, which was longer than the length of the suture attached to the proximal-most release pin, the proximal-most release pin would proximally withdraw from the opening of rings (725), thereby allowing a proximal portion of the stent to expand. However, since the sutures associated with the middle release pin and the distal-most release pin are longer than the first distance and the suture associated with the proximal-most release pin, the middle and distal-most release pins are not proximally withdrawn when the rod is only withdrawn a first distance.

If a user were to continue to proximally withdraw the rod to a second distance, the middle release pin would proximally withdraw from the opening of rings (725), thereby allowing a mid-section of the stent to expand. Since the suture associated with the distal-most release pin is longer than the second distance and the suture associated with the middle release pin, the distal-most release pin would not proximally withdraw when the rod is only withdrawn a second distance. However, when the rod is further withdrawn a third distance, the distal-most release pin would then withdraw from the openings of the distal-most rings, thereby allowing a distal portion of the stent to expand.

Of course, any length suture may be associated with any release pin in the stent. For example, in the configuration depicted in FIG. 7, if a user wanted to expand the mid-section of the stent before the proximal and distal portions of the stent, the suture associated with the middle release pin would be made shorter than the sutures associated with the distal and proximal release pins. Additionally, while three sutures are shown if FIG. 7, the rod may comprise any number of sutures. In some embodiments, the rod comprises a separate suture for each release pin. Thus, if the stent comprised five release pins, the rod would comprise five sutures.

Furthermore, the configuration depicted in FIG. 7 may include additional rods in connection with the release pins. For example, a first rod can be connected by a suture to the proximal and mid-section release pins and a second rod may be attached by a suture to the distal release pin. The rods may be proximally or distally withdrawn to remove the release pins and allow the stent to expand. In some embodiments, the outer diameter of each release pin is slightly smaller than the inner diameter of each fastener, such that a tight fit may be achieved between the release pin and the lumen of the fastener. If release pins are not utilized and one or more rods pass through the lumens of the fasteners, the outer diameter of each rod may be slightly smaller than the inner diameter of each fastener.

Any stent known in the art may be used in accordance with the present disclosure. That is, any stent may be configured to include a plurality of fasteners. Various designs known in the art may be used for the stent structure. For example, the stent structure may be made with serpentine rings interconnected with longitudinal structural members. The stent structure may be fabricated from a cannula, and may have longitudinal segments of laterally interconnected closed cells, as disclosed in U.S. Pat. Nos. 6,231,598, and 6,743,252 which are incorporated herein by reference in their entirety.

In other embodiments, the stent structure may be a wire frame constructed from a plurality of wire stent segments as disclosed in U.S. Pat. No. 5,195,984, the entire contents of which are incorporated herein by reference, or the stent be made from a braided framework of wire filaments. Other stent structures are also possible.

Regardless of the structure of the stent, it has a reduced diameter delivery state in which it may be advanced to a target location within a vessel, duct, or other anatomical site. The stent additionally has an expanded deployed state in which it may be configured to apply a radially outward force upon a vessel, duct, or other target location, e.g., to maintain patency within a passageway.

The stent may comprise one or more of a variety of materials, such as nitinol, stainless steel, cobalt-chrome alloys, amorphous metals, tantalum, platinum, gold, titanium, and any combination thereof. The stent may also comprise non-metallic materials, such as various thermoplastics or other polymers. In some embodiments, the stent comprises elastic, super-elastic, or spring-metal alloys, such as nitinol, such that it may compress under force, and, when unrestrained, will tend to return to its expanded configuration in a spring-like manner. Any of the foregoing materials may also be included in other components disclosed herein, such as the fasteners, rods, outer tubes, etc. For example, in some embodiments, the fasteners may comprise nitinol, stainless steel, a polymeric material, or any other biocompatible material.

Any known delivery system or delivery catheter may be used to deliver the presently disclosed stents to a target site. However, as opposed to traditional delivery systems, a delivery system used to deliver and deploy the presently disclosed stents need not include an outer stent restraining sheath.

In some embodiments, the delivery device includes a handle and an outer tube having a proximal and distal end. The proximal end of the outer tube is connected to the distal end of the handle. The outer tube comprises a lumen and a rod disposed therein. A distal end of the rod protrudes from the distal end of the outer tube and a proximal end of the rod passes into the handle. A stent comprising a plurality of fasteners may then be compressed so that openings in the fasteners align and the distal end of the rod may then be passed through the openings to hold the stent in its compressed configuration. In some embodiments, a guide wire may be loaded through a distal end opening of the rod and emerge from a proximal portion of the handle. This delivery system may then be used to place the stent at the target location in the body and once there, the rod may be proximally withdrawn to allow the stent to expand. The fasteners remain connected to the stent after deployment and might be useful when retrieving the stent at a later time or they may provide additional friction forces that help prevent migration of the stent within a lumen.

In some embodiments, the positioning of the stent may be performed using fluoroscopic guidance. Moreover, one or more of the components of the stent and/or delivery system may comprise a radiopaque marker to facilitate positioning of the stent. In some embodiments, at least one radiopaque marker is disposed on the stent to facilitate positioning at a target location, such as within a stenosed region of a vessel.

Again, the manner by which the rod is proximally withdrawn is not limited and any known techniques may be used. In some embodiments, a proximal end of the rod may simply be grasped and pulled by the physician. In other embodiments, the proximal end of the rod may be attached to an element of the handle and the rod is proximally withdrawn by proximally withdrawing the element of the handle. Additionally, the handle may comprise a trigger-type mechanism and each time the trigger is depressed, the rod may be proximally withdrawn incrementally. For example, US 2009/0171433 (the disclosure of which is incorporated into the present application in its entirety) discloses a handle comprising a trigger and each time the trigger is pulled/depressed, an outer sheath is proximally withdrawn incrementally. Such a device may be modified to be used with the presently disclosed rod instead of an outer sheath, wherein each time the trigger is pulled, the rod is proximally withdrawn a predetermined distance.

As may be deduced from the present disclosure, the overall size of the introduction system used to place the stent at the target location is reduced since an outer sheath is not required to hold the stent in the radially compressed configuration and can therefore be excluded. By using the rod and fasteners disclosed herein, the stent can be tightly compressed, more so than using a traditional sheath, and high deployment forces commonly associated with delivery systems comprising outer sheaths can be eliminated. The presently disclosed stent/fastener combination can be used in a variety of applications, such as by endoscopists in hospital/clinical settings to treat diseases of the esophagus, colon, bile duct and/or diseases in other body lumens.

All of the devices and methods disclosed and claimed herein can be made and executed without undue experimentation in light of the present disclosure. While this invention may be embodied in many different forms, there are described in detail herein specific exemplary embodiments. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a fastener" is intended to include "at least one fastener" or "one or more fasteners."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages.

It is therefore intended that such changes and modifications be covered by the appended claims.

What is claimed is:

1. A stent delivery system including a self-expanding stent, the stent comprising a proximal portion, a mid-section, and a distal portion, wherein one or more of the proximal portion, mid-section, and distal portion comprises a plurality of fasteners, the plurality of fasteners being disposed about a periphery of the stent and woven through one or more open cells of the stent, wherein each fastener of the plurality of fasteners comprises an opening, wherein a rod of the delivery system comprises a plurality of release pins attached by sutures to a distal rod portion, wherein each release pin of the plurality of release pins is disposed through the openings of two or more of the fasteners, thereby holding the stent in a radially compressed configuration.

2. The stent delivery system of claim 1, wherein when the stent is in a radially compressed configuration, the openings of each fastener align or become concentric in a lumen of the stent.

3. The stent delivery system of claim 1, wherein a length of at least one suture is longer than a length of the other sutures.

4. The stent delivery system of claim 1, wherein the proximal portion comprises a proximal plurality of fasteners, the distal portion comprises a distal plurality of fasteners, and the mid-section comprises a mid-plurality of fasteners.

5. The stent delivery system of claim 4, wherein when the stent is in a radially compressed configuration, each opening of each fastener of the proximal plurality are in alignment, each opening of each fastener of the mid-plurality are in alignment, and each opening of each fastener of the distal plurality are in alignment.

6. The stent delivery system of claim 5, wherein a first release pin is disposed through the openings of the fasteners of the distal plurality, a second release pin is disposed through the openings of the fasteners of the mid-plurality, and a third release pin is disposed through the openings of the fasteners of the proximal plurality.

7. The stent delivery system of claim 6, wherein the first release pin is attached to a distal portion of a rod by a first suture, the second release pin is attached to the distal portion of the rod by a second suture, and the third release pin is attached to the distal portion of the rod by a third suture.

8. The stent delivery system of claim 7, wherein the first, second, and third sutures comprise different lengths.

9. A method of deploying a stent at a target location comprising: providing a stent in a radially compressed configuration, a distal portion of the stent comprising a first plurality of fasteners, a mid-section of the stent comprising a second plurality of fasteners, and a proximal portion of the stent comprising a third plurality of fasteners, each fastener comprising an opening, wherein the openings of each fastener of the first plurality of fasteners are in alignment, the openings of each fastener of the second plurality of fasteners are in alignment, and the openings of each fastener of the third plurality of fasteners are in alignment, and further wherein a first release pin is disposed through the openings of each fastener of at least the first plurality of fasteners and a second release pin is disposed through the openings of each fastener of at least the third plurality of fasteners, the first release pin being attached to a distal portion of a rod by a first suture and the second release pin being attached to the distal portion of the rod by a second suture; placing the stent at the target location; withdrawing the rod, thereby causing the first and second release pins to withdraw from the openings of the fasteners; allowing the stent to expand; and deploying the stent at the target location.

10. The method of claim 9, wherein the first suture comprises a first length and the second suture comprises a second length that is different than the first length.

11. The method of claim 10, wherein the stent comprises a third release pin disposed through the openings of each fastener of the second plurality of fasteners, the first release pin being disposed only through the openings of each fastener of the first plurality of fasteners and the second release pin being disposed only through the openings of each fastener of the third plurality of fasteners, the third release pin being attached to the distal portion of the rod by a third suture, the third suture having a third length that is different than the first and second lengths, wherein proximally withdrawing the rod allows the distal portion, mid-section, and proximal portion of the stent to expand separately.

* * * * *